US011730358B2

(12) United States Patent
Tai et al.

(10) Patent No.: US 11,730,358 B2
(45) Date of Patent: Aug. 22, 2023

(54) TEAR FLOW MEASUREMENT DEVICE

(71) Applicants: California Institute of Technology, Pasadena, CA (US); University of Southern California, Los Angeles, CA (US)

(72) Inventors: Yu-Chong Tai, Pasadena, CA (US); Nicholas E. Scianmarello, Pasadena, CA (US); Mark S. Humayun, Glendale, CA (US)

(73) Assignees: California Institute of Technology, Pasadena, CA (US); University of Southern California, Los Angeles, CA (US)

( * ) Notice: Subject to any disclaimer, the term of this patent is extended or adjusted under 35 U.S.C. 154(b) by 667 days.

(21) Appl. No.: 16/786,377

(22) Filed: Feb. 10, 2020

(65) Prior Publication Data
US 2020/0260946 A1  Aug. 20, 2020

Related U.S. Application Data

(60) Provisional application No. 62/806,182, filed on Feb. 15, 2019.

(51) Int. Cl.
*A61B 3/10* (2006.01)
*G01N 30/02* (2006.01)
*G01G 19/00* (2006.01)
*G01F 22/00* (2006.01)
(Continued)

(52) U.S. Cl.
CPC ............ *A61B 3/101* (2013.01); *A61B 5/6821* (2013.01); *A61B 5/6867* (2013.01);
(Continued)

(58) Field of Classification Search
CPC ..... A61B 3/101; A61B 5/6821; A61B 5/6867; A61B 10/0045; A61B 2010/0067;
(Continued)

(56) References Cited

U.S. PATENT DOCUMENTS 3,861,396 A * 1/1975 Vaillancourt ......... A61L 29/085
604/129
4,531,943 A * 7/1985 Van Tassel ......... A61M 25/1011
604/523
(Continued)

OTHER PUBLICATIONS

PCT/US2020/017480 , "International Preliminary Report on Patentability", dated Aug. 26, 2021, 8 pages.
(Continued)

*Primary Examiner* — William R Alexander
*Assistant Examiner* — Sharrief I Broome
(74) *Attorney, Agent, or Firm* — Kilpatrick Townsend & Stockton LLP

(57) ABSTRACT

A lacrimal tear flow measurement device, and methods of manufacture and use, are described that includes a polymer microcapillary tube or similar structure having at least one end coated on the outside with soft silicone rubber and one end treated on the inside to be hydrophobic. The hydrophobic end keeps liquid from escaping or entering that end while allowing air to pass. The rest of the tube's insides may be hydrophilic or a neutral hydrophobe. As a Schirmer's test strip replacement, the entrance end of the device can be touched to the lacrimal lake of a patient's eye to collect suck up, or merely collect, tear fluid within the collection tube for weighing, volume measurement, or other analysis. Long-term collection devices for wear between doctors' visits can have a bypass channel allowing liquid to flow back onto the eye.

26 Claims, 8 Drawing Sheets

(51) Int. Cl.
*G01N 1/10* (2006.01)
*A61B 5/00* (2006.01)
*A61B 10/00* (2006.01)
*G01N 33/487* (2006.01)

(52) U.S. Cl.
CPC .......... *A61B 10/0045* (2013.01); *G01F 22/00* (2013.01); *G01G 19/00* (2013.01); *G01N 1/10* (2013.01); *G01N 30/02* (2013.01); *G01N 33/4875* (2013.01); *A61B 2010/0067* (2013.01); *G01N 2030/027* (2013.01)

(58) Field of Classification Search
CPC .......... G01F 22/00; G01G 19/00; G01N 1/10; G01N 30/02; G01N 33/4875; G01N 2030/027
See application file for complete search history.

(56) References Cited

U.S. PATENT DOCUMENTS

| | | | |
|---|---|---|---|
| 4,635,488 A | 1/1987 | Kremer | |
| 5,849,368 A | 12/1998 | Hostettler et al. | |
| 6,186,974 B1 * | 2/2001 | Allan | A61F 9/00781 604/30 |
| 2002/0198453 A1 * | 12/2002 | Herrick, II | A61B 17/12159 600/407 |
| 2006/0188410 A1 * | 8/2006 | Ishida | A61B 10/0051 422/400 |
| 2014/0309554 A1 * | 10/2014 | Roy | A61B 10/0045 600/581 |
| 2014/0342371 A1 * | 11/2014 | Holmes | A61B 5/150343 435/7.1 |
| 2016/0367806 A1 * | 12/2016 | Kahook | A61N 1/37205 |
| 2016/0374648 A1 * | 12/2016 | Asvadi | G02C 7/04 600/573 |
| 2017/0252019 A1 | 9/2017 | Kim et al. | |
| 2018/0104514 A1 * | 4/2018 | Gertner | A61H 23/0245 |

OTHER PUBLICATIONS

PCT/US2020/017480, "International Search Report and Written Opinion", dated Apr. 16, 2020, 9 pages.

* cited by examiner

TEAR FLOW MEASUREMENT DEVICE

CROSS-REFERENCES TO RELATED APPLICATIONS

This application claims the benefit of U.S. Provisional Application No. 62/806,182, filed Feb. 15, 2019, the contents of which are hereby incorporated by reference in its entirety for all purposes.

STATEMENT AS TO RIGHTS TO INVENTIONS MADE UNDER FEDERALLY SPONSORED RESEARCH AND DEVELOPMENT

NOT APPLICABLE

BACKGROUND

1. Field of the Invention

The present application generally relates to instruments for taking samples of tear or lachrymal fluid. Specifically, it relates to biocompatible microtubes using hydrophobic and other surface treatments to trap tear liquid for measurement.

2. Description of Related Art

Dry eye is a condition in which a person doesn't have enough quality tears to lubricate and nourish the eye. It is a widespread disease affecting 4.9 million Americans over fifty years of age. Tears are necessary for maintaining the health of the front surface of an eye and for providing clear vision. Dry eye is common, and often a chronic problem, amongst the general population, particularly in older adults.

Most common treatments for dry eye include: i) administration of artificial tears/medications/ointments, and/or ii) a punctal occlusion with a plug that cause the tears to remain in the eye longer.

Punctal plugs come in two forms: temporary and permanent. Temporary punctal plugs are typically made of collagen and dissolve over time. Permanent punctal plugs are typically made of silicone and range in diameters from 0.2 to 0.4 millimeters (mm).

Before prescribing artificial tears or applying plugs, an eye doctor performs an assessment of a patient's eyes. One would like to know the flow rate of lacrimal liquid secreted by the lacrimal glands onto the eye. However, there is a lack of reliable and precise technologies for dry-eye diagnostics, including tear flow measurement.

Schirmer's test involves holding an absorbent filter paper strip to the lacrimal lake of a subject's eye. It is kept there for upwards of five minutes. Liquid wicks its way up the strip, turning the strip a slightly different color from the wetness. The farther the liquid creeps, the moister the eye. Commonly, young people moisten the strip about 15 mm, while elderly people moisten only 10 mm.

The Schirmer test has not improved much for over a century. This is unfortunately because it has its drawbacks. The touch of paper to one's eye sometimes causes irritation and reactive tears in response. This results in a reading that is too high. To counter the irritation that causes the reactive tear reflex, a topical anesthetic may be applied. But then the anesthetic may affect the tear flow measurement results. Further, the filter paper used for Schirmer strips largely composed of randomly sized interstitial spaces between fibers. One piece of paper may transport liquid faster or in greater quantities than another piece of paper. That is, calibration between strips is an issue.

There is a need in the art for better tear flow measurement devices and techniques in order to help those suffering from dry eye.

BRIEF SUMMARY

Generally, a biocompatible, polymer microcapillary is treated so it can trap liquid inside that seeps into one end. It does this by having a hydrophobic inner surface treatment for a short portion at the opposite end. The rest of the inner surface is either neutral or hydrophilic. Lacrimal tear liquid is allowed to seep into the microcapillary at the entrance end while air is pushed out of the opposite, exit end. At the 1- to 1000-micron (μm) scale involved, the hydrophobic surface at the exit end exerts enough influence on any nearby liquid to prevent its escape out of the exit end. Meanwhile, air passes unencumbered by the treated surface out the exit end.

The entrance end, and sometimes the entire microcapillary, is coated with a soft, cushiony silicone rubber. This minimizes irritation of the eye or eyelid from the end of the harder microcapillary. In contrast, the microcapillary itself is made of a firmer plastic that more stably holds its surface hydrophobicity and hydrophilicity over time than silicone rubber.

The tear secretion measurement device can be made by taking a tube made from a naturally hydrophilic polymer and exposing one end to a burst of oxygen plasma to make the end hydrophobic. The tube can then be inserted into a sleeve of silicone rubber. The entrance end of the tube need only be held to the lacrimal lake (near the bottom eyelid) of a patient in order to suck up the moisture there.

A long tube can be rolled into a flat coil, leaving enough room in the center for a patient's cornea. The coil, preferably fused together to make a ring and shaped into a sclera lens, is implanted under the conjunctiva of a patient. It can be left in the patient's eye for days, or even weeks, to slowly collect tear fluid. It may have a calibrated bypass section that allows liquid to enter the whole device and then release excess fluid to the eye. The collected fluid can then be analyzed at a next visit to the doctor's office.

Some embodiments of the present invention are related to a tear secretion measurement apparatus including a polymer capillary tube having an inner diameter between 1 micron to 1000 microns (μm), the capillary tube having a hydrophobic inner surface localized at an exit end of the capillary tube and a hydrophilic or neutral hydrophile inner surface throughout a remainder of the capillary tube extending to an entrance end of the capillary tube. The tear secretion measurement apparatus also includes a silicone rubber covering over an outer diameter of the capillary tube at least at the entrance end.

The hydrophobic inner surface can extend between 1 μm to 5000 μm from the exit end, thereby sufficient to allow air to pass but prevent tear fluid from passing through the exit end. The hydrophobic inner surface can extend between 0.001% to 10% of a length of the capillary tube from the exit end. The inner diameter of the polymer capillary tube can be between 200 μm and 400 μm. The polymer capillary tube and the silicone rubber covering can be biocompatible. The polymer capillary tube can be made from parylene C, parylene HT, polyamide, polyether ether ketone (PEEK), polyethylene, or polypropylene. The length of the capillary tube can be between 2 millimeters to 50 millimeters (mm) or more, and the remainder of the inner surface can be hydrophilic. The silicone rubber covering can be a pre-formed silicone tube into which the polymer capillary tube was inserted. The silicone rubber covering can be produced by dip coating the polymer capillary tube in diluted, uncured silicone rubber and allowing it to cure. The silicone rubber covering can extend over an entire outer diameter of the capillary tube from the entrance end to the exit end. The capillary tube can be transparent or translucent, and the apparatus can further include volume measurement markings on the outer diameter of the capillary tube.

There can be a bypass channel extending from the entrance end and around an outside of the capillary tube to the exit end, the bypass channel configured to allow a predetermined ratio of liquid to bypass the polymer capillary tube. The polymer capillary tube can be wound into a coil, the coil having an inner diameter between 11 millimeters and 24.5 millimeters (mm). The wound capillary tube can be fused to form a solid coil.

Some embodiments are related to a method of manufacturing a tear secretion measurement apparatus. The method can include providing a polymer capillary tube having an inner diameter between 1 micron to 1000 microns ($\mu m$), treating an inner surface at an exit end of the capillary tube to be hydrophobic, and covering an entrance end of the capillary tube with a silicone rubber covering.

An entire inner surface of the polymer capillary tube could have been a hydrophilic or neutral hydrophile surface before the hydrophobic treating. The method can include modifying a remainder of the inner surface extending to the entrance end of the capillary tube to be hydrophilic by exposing to oxygen plasma or flushing with an oxidizing acid. The hydrophobic treating includes a treatment selected from the group consisting of coating with parylene HT, exposing to xenon difluoride or silanating gas, and treating with plasma.

The method can include forming a bypass channel extending from the entrance end and around an outside of the capillary tube to the exit end, the bypass channel configured to allow a predetermined ratio of liquid to bypass the polymer capillary tube.

Some embodiments are related to a method of measuring tear secretion, the method including providing a polymer capillary tube having an inner diameter between 1 micron to 1000 microns ($\mu m$), the capillary tube having a hydrophobic inner surface localized at an exit end of the capillary tube and a hydrophilic or neutral hydrophile inner surface throughout a remainder of the capillary tube extending to an entrance end of the capillary tube, contacting the entrance end to a lacrimal lake of a subject's eye, waiting for tear liquid from the lacrimal lake to be drawn into the capillary tube, and measuring an amount of tear liquid that was drawn into the capillary tube.

Measuring the amount can include determining a volume of or weighing the drawn tear liquid. The method can include performing liquid chromatography on the drawn tear liquid.

The polymer capillary tube can be wound into a coil, the coil having an inner diameter between 11 millimeters and 24.5 millimeters (mm). The method can further include implanting the coil partially under a conjunctiva and over a sclera of the subject's eye such that the exit end is above the lacrimal lake of a patient's eye.

The method can further include providing a bypass channel extending from the entrance end and around an outside of the capillary tube to the exit end, the bypass channel configured to allow a predetermined ratio of liquid to bypass the polymer capillary tube. It can also include implanting the capillary tube as a straight or bent plug within a nasolacrimal duct of the subject's eye.

DETAILED DESCRIPTION

Generally, tear flow measurement devices are described in which an end of a small tube with an inner diameter between 1 micron to 1000 microns ($\mu m$) has been treated to be hydrophobic. At that scale, forces between the hydrophobic surface and the liquid meniscus dominate other forces and determines whether liquid is held back or passes. While allowing gaseous air to pass, the hydrophobic treatment holds back liquid inside the tube from exiting and prevents liquid from outside entering the exit end.

A lacrimal tear sampling device, or a microfluidic tube Schirmer-strip replacement, is made up of material that can quickly sample tear fluid, and each "tube strip" has the capacity to sample approximately a few micrograms ($\mu g$) of tear fluid. Precise weight measurements of the collected sample can be obtained for quantification. Various materials and form factors of the strips can be tested to achieve optimal performance. Encapsulation of the strip might be added to help handling and improve the collection process during tear sampling. Sealing capability of the strip can be enhanced in order to reduce evaporation during weight measurement.

Such a device can have the capability to reliably and precisely collect tear liquid from a patient. Used in conjunction with other instruments, it can help quantify tear production and assess the chemical aspects or other quality of the tears.

The tear device can be put through a portable analytical system, such as a liquid chromatography machine, to analyze the chemical composition of the collected tears. At the beginning of a clinical measurement, a significant amount of existing tear is first removed. Then, at a first time point, the first tear sample is collected and measured. Subsequent measurements can be made with new microfluidic tubes at different time intervals. A plot of tear production vs. time can be generated.

Short-term and/or long-term tear collecting devices can be used clinically for sampling patients' tears.

Short-Term Tear Collecting Tube Device

A short-term tear collecting device's fiber-like geometry can be straight, curved, winding/twisting, etc. depending on its placement. For example, the tube should have a curvature matching the curvature of the eyeball if it is placed inside the inferior eyelid for a few tens of minutes. As another example, the tube can be a relatively straight tube with one end placed between the eyelid and the eye (inferior fornix) for short-term tear collection for seconds to a few minutes. The tube can also have a winding or twisting geometry to increase the total volume capacity for tear collection.

The tube can have a diameter sized to collect all the tear fluid produced short-term wise in an eye, depending on the tear-collecting time. For examples, a typical diameter can range from 10-3,000 µm.

Figure 1A:
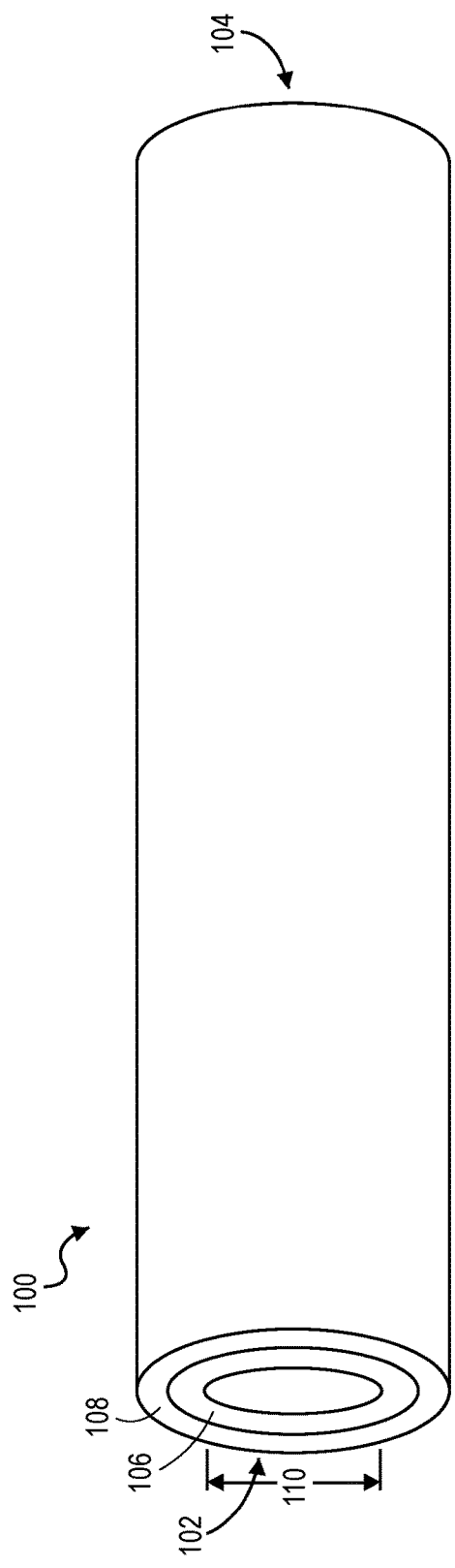
FIG. 1A illustrates a tear secretion measurement device having a silicone rubber covering along its entire length in accordance with an embodiment.
Figure 1B:
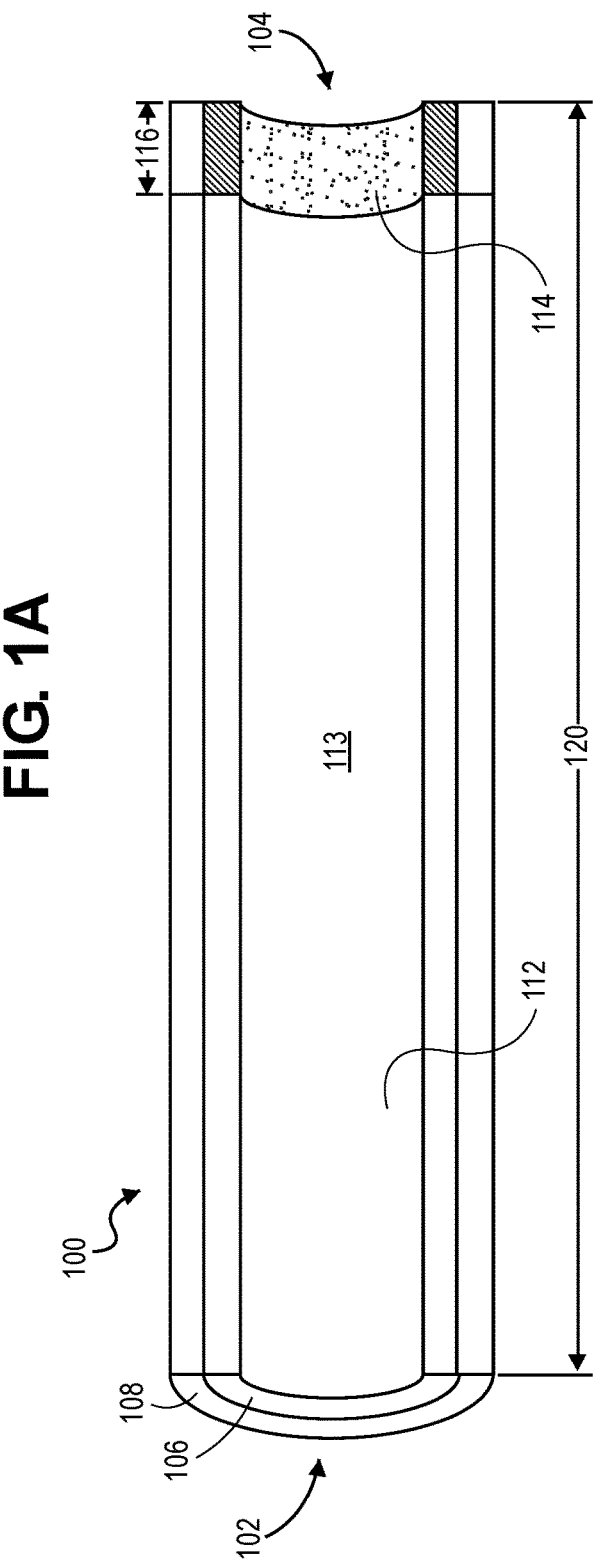
FIG. 1B illustrates a longitudinal cross section of the device of FIG. 1A.

FIGS. 1A-1B illustrate a tear flow measurement device having a soft silicone rubber covering 108 along its entire length 120. Device 100 includes biocompatible polymer capillary tube 106 with inner diameter 110 between 1 and 1000 µm. Capillary tube 106 has entrance end 102 and exit end 104.

Some embodiments can have an inner diameter between 200 µm and 400 µm, 100 µm and 500 µm, 1 µm and 3000 µm, or other ranges depending upon the specific application. As stated above, the capillary tube can be straight (as shown), curved, bent, or take on a variety of other shapes.

The capillary tube can be made out of parylene C, parylene HT, polyamide, polyether ether ketone (PEEK), polyethylene, polypropylene, or other biocompatible polymers that will stably hold their hydrophobicity or hydrophilicity for long periods.

In some embodiments, a soft outer coating can be added to a device by dip-coating the device. In the case of soft platinum-catalyzed silicones, the uncured mixture may be thinned with solvents such as hexane, and the part is dipped into the low viscosity silicone. Controlling the viscosity of the mixture controls the thickness of the coating.

Coatings may also be added by spray coating. Silicone may be diluted in hexane and ultrasonically spray coated on the device.

The soft coating may also be slipped over the device. The tube with the soft coating is chosen to have an inner diameter identical or slightly smaller than the outer diameter of the device. This soft tube (coating) is first soaked in a compatible organic solvent, such as isopropanol, acetone, or hexane, to cause the soft tube to swell. The now swollen tube's inner diameter would have increased due to the absorbed solvent and would fit over the inner tube. The solvent then evaporates and compress onto the inner tube.

The entire outer circumference of capillary tube 106 is coated with silicone rubber covering 108, from entrance end 102 to exit end 104. The covering was formed by taking a pre-formed silicone rubber tube, expanding it by having it absorb a liquid, inserting the polymer capillary through one end, then allowing the liquid to evaporate. Like a sponge, the silicone rubber tube shrinks when the liquid within it evaporates out. In this case, the shrinking makes a tight fit around the outer circumference of the capillary tube.

Another process for soft coating is to place the device in a large mold to over-mold the soft silicone coating.

Capillary tube 106 has inner surface 113 extending from entrance end 102 to exit end 104. Localized near exit end 104, the inner surface is hydrophobic inner surface 114. The localized section extends a length 116 from exit end 104 into the tube. The length can be between 2 millimeters to 50 millimeters (mm), 100 mm, 150 mm, 200 mm, 300 mm, 400 mm, 500 mm, or other lengths in accordance with the required reservoir volume for storing tear fluid. The capillary tube is not shown to scale in the figure.

The length of localized hydrophobicity can be 1 µm to 5000 µm, depending upon the inner diameter of the capillary tube (see equations above). Another measure is the percentage of length 116 over the entire length of the capillary tube 120. The localized percentage of hydrophobicity can be between 0.001% and 10% of the length of the capillary tube.

The inner surface of a tube can be made hydrophobic by coating it with parylene-HT, which is inherently hydrophobic. The length of the coated region can be controlled by warming or cooling the device during the deposition. It is thought that the temperature of the device changes the mobility of the parylene monomer before polymerization on its surface.

The surface may also be made hydrophobic by exposure to $XeF_2$ gas or silanating gases such as hexamethyldisilazane (HMDS). For hydroxyl bonds on the surface, HMDS leaves a methylated surface which can be quite hydrophobic. Using oxygen plasma to promote hydroxyl bonds on the surface of parylene or silicone, and then treating with HMDS can create a highly hydrophobic surface. Oxygen plasma breaks bonds in polymers and oxidizes the surface. The resultant surface forms a hydroxyl layer in contact with the air, which is hydrophilic. This effect is magnified by the roughening impact of oxygen plasma.

The inner surface of the tube may also be flushed with an oxidizing acid such as nitric acid, or nitric acid in combination with hydrogen peroxide. This flush will oxidize the surface and result in a hydroxyl layer similar to oxygen plasma, i.e., result in a hydrophobic surface.

A remainder 112 of the inner surface 113 in the figures is hydrophilic or neither hydrophilic nor hydrophobic, i.e., a neutral hydrophile. A "remainder" of the inner surface is substantially all of the inner surface that is not hydrophobic.

If the tube used was not inherently hydrophilic, surface treatments mentioned above may be applied.

For hydrophilic surfaces, one can treat the surface with a plasma such as $CF_4$ or $C_2H_2$ or a combination thereof. Such plasmas can create a surface with $CF_x$ bonds on the surface that are hydrophilic. Coupling this with micron scale or nano scale roughness can result in a superhydrophobic surface.

The hydrophobic tube end can also be achieved by assembling a hydrophobic tube onto the end of the device. This hydrophobic tube can be retained by the soft outer tube with an interference fit.

For a short-term collector, the length of the tube collector, engineered together with its diameter, should be enough to collect all tear in an eye when its entrance is in contact with the tear for a desirable short period of time, such as from a few seconds to a day. For example, a typical length can range from sub-millimeters to a few meters.

The interior surface of the tube collector can be entirely hydrophilic. In other words, the water contact angle of the interior surface can range from a few degrees to 90±20 degrees so that the meniscus force of the tear inside the tube will dominate the tear flow into the tube. At these small scales, the result is a strong suction mechanism for tear fluid to go inside the tube.

The tube collector can work independently by placing the tube at the right placement with respect to a tear, or the tube can work with a supporting/holding tool to facilitate manual handling. For example, the tube can be twisted around an inserter that can easily be handled by a hand.

The whole tube, including both ends of the entrance and exit, can be coated with a soft material as shown, including but not limited to collagen or soft silicone, to ensure eye comfort.

In some respects, the short-term tube embodiment can be taken to have three or so parts: a hydrophilic tube to pull liquid into the tube, a hydrophobic end to allow air to exit and retain liquid, and a soft outer coating that may be used on the hydrophilic tip placed in contact with the eye, or throughout the whole tube.

The contact angles for the hydrophilic side should be anything less than 90°, such as 20°-89°, 40°-89°, or otherwise.

The contact angles on the hydrophobic side should include anything greater than 90°, such as 91°-150°, which represents the range of manufacturable hydrophobic contact angles. The hydrophobic section can be 1 µm-5 mm in length in some embodiments.

The inner diameter of the tube can have a range from 1 µm-1 mm. The diameter of the tube along with the contact angle is used to determine the suction force:

$$F = 2r\pi\gamma\cos\theta$$
$$p = \frac{2\gamma\cos\theta}{r}$$

where F is the force, p is the pressure, r is the radius, y is the liquid-air surface tension, and θ is the contact angle. For a tube with a circular cross section, its hydraulic resistance is given by:

$$R = \frac{8\mu L}{\pi r^4}$$

The flow rate, Q, through the tube is given by:

$$Q = \frac{p}{R} = \frac{\pi r^3 \gamma \cos\theta}{4\mu L}$$

where L is the length, and µ is the fluidic viscosity. The contact angle and radius of the pipe is chosen to suck up the given volume in a given amount of time. In some embodiments, the device can be designed to suck a minimum of 10 µL and a maximum of 100 µL of fluid. The tear accumulation section of the device should be large enough to accommodate the volume, V, and therefore would have a maximum length given by $L=V/\pi r^2$.

For a desired collection volume, V, and time, t, the largest inner radius for the short-term tear collector for the device is:

$$r \le \left(\frac{4\mu V^2}{t\pi^2 \gamma \cos\theta}\right)^{1/5}$$

Figure 2A:
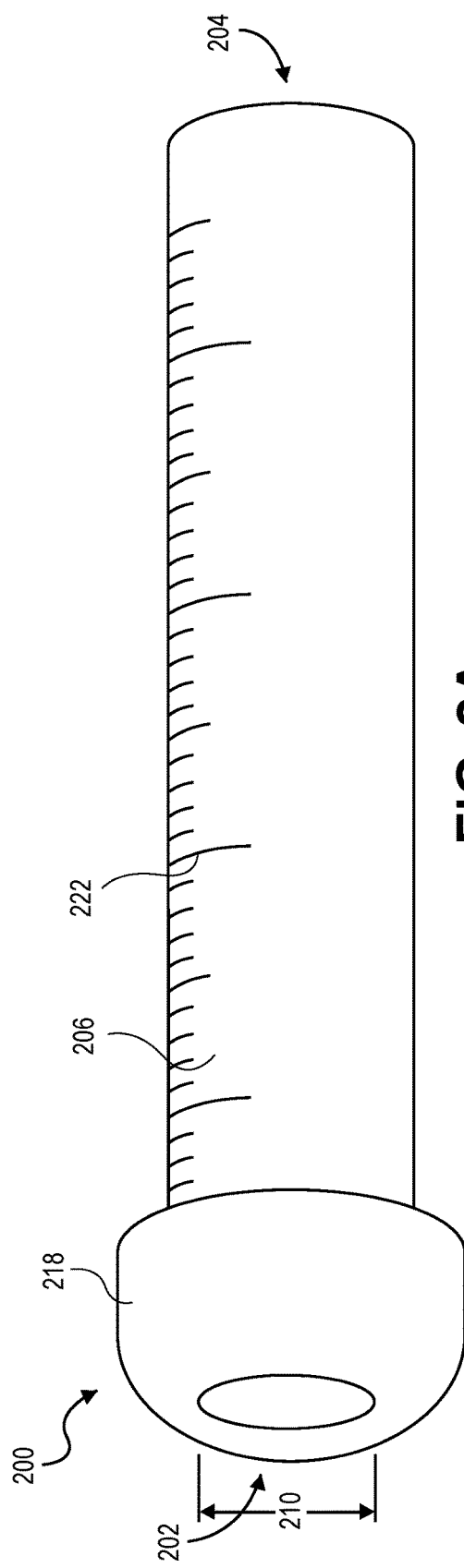
FIG. 2A illustrates a tear secretion measurement device having a silicone rubber tip in accordance with an embodiment.
Figure 2B:
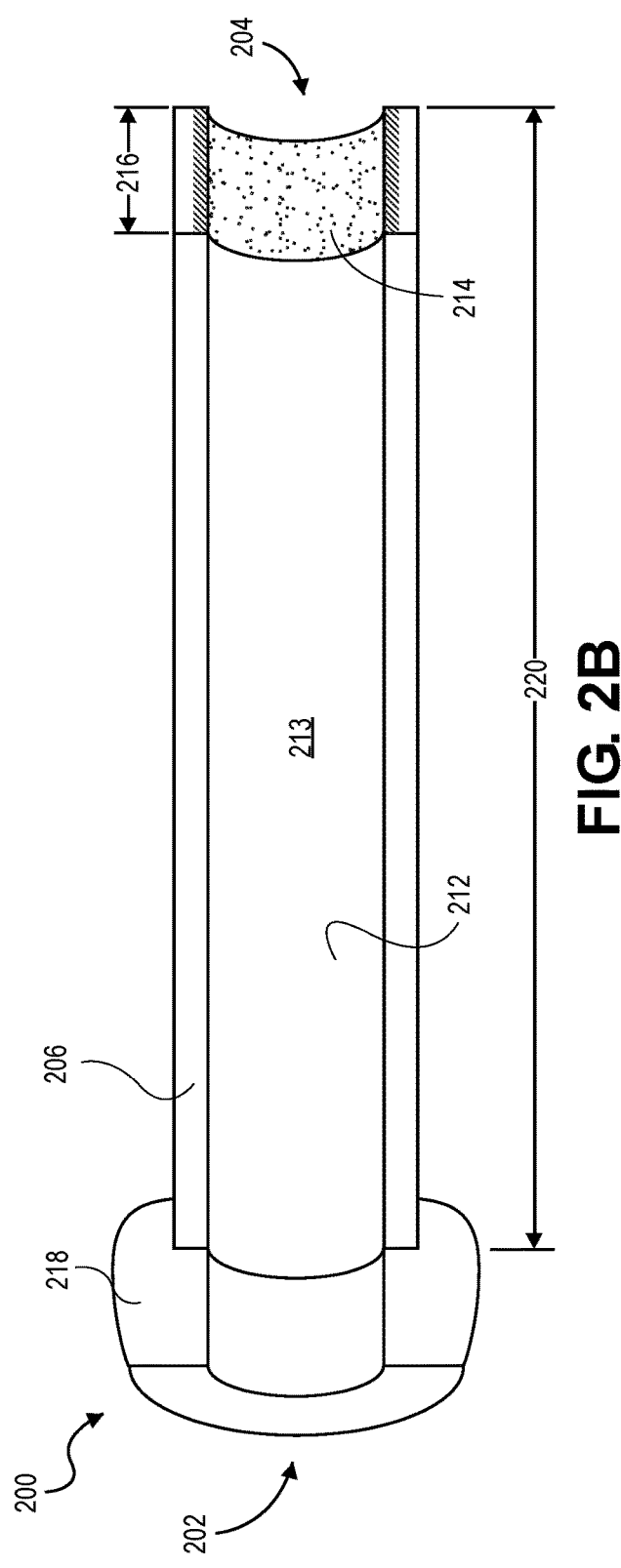
FIG. 2B illustrates a longitudinal cross section of the device of FIG. 2A.

FIGS. 2A-B illustrate a tear secretion flow measurement device having silicone rubber just at its tip. Device 200 includes biocompatible capillary tube 206 having entrance end 202 and exit end 204. Its inner diameter 210 and length 220 can have the same ranges as in the previous embodiment.

Only a small tip portion near entrance end 202 of capillary tube 206 is coated with silicone rubber covering 218. The covering near the tip decreases the sharpness of the end of the capillary and lessens irritation to a subject's eye.

Inside the capillary tube is inner surface 213, extending to the entrance area, but not necessarily including an inner surface created by silicone rubber covering 218. Exit end 204 has localized hydrophobic inner surface 214 extending a length 216 from exit end 204. The balance of inner surface 213 is hydrophilic or has neutral hydrophilicity.

Figure 3:
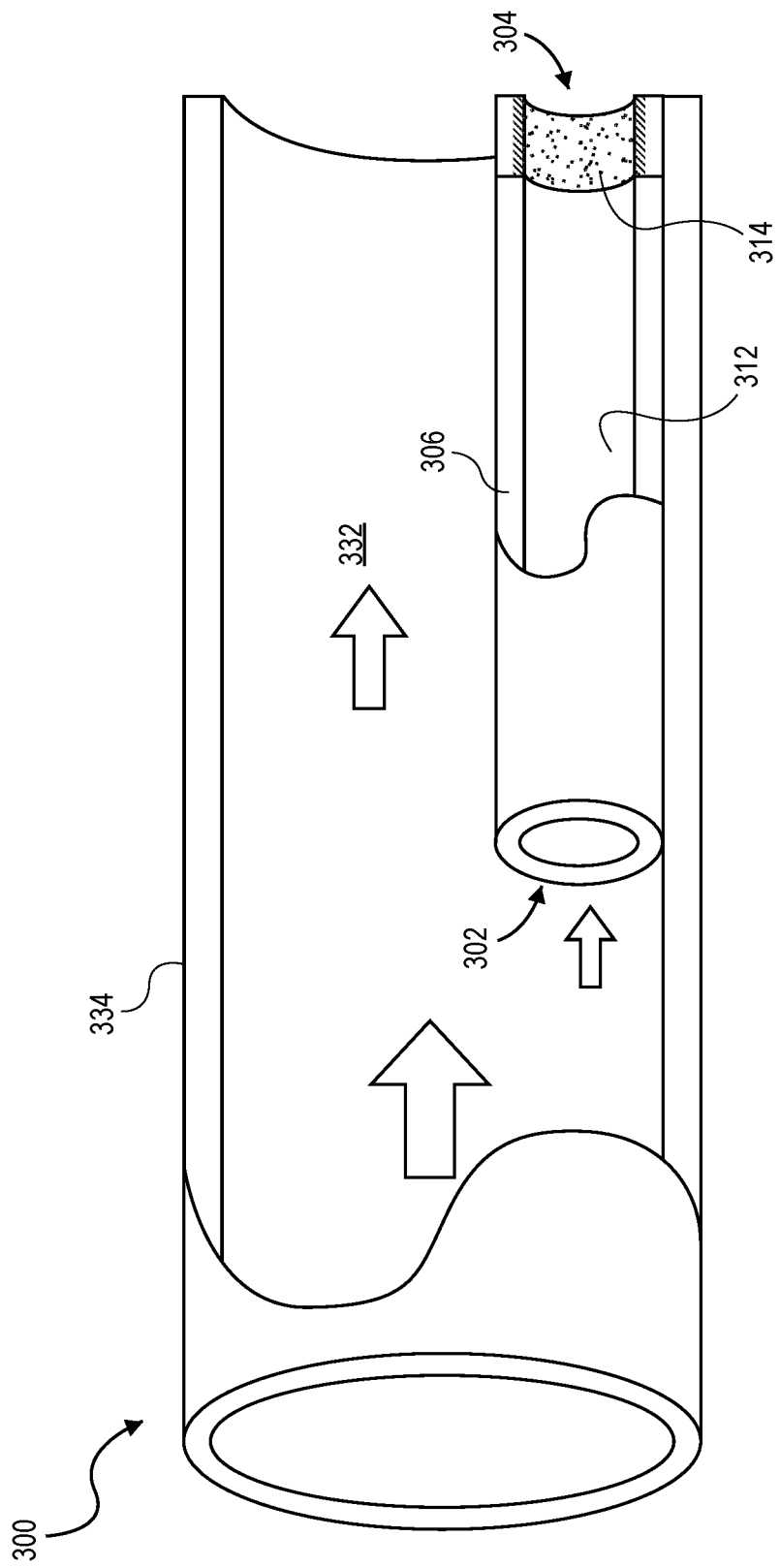
FIG. 3 illustrates a bypass channel to a tear secretion measurement device and cross section cutout in accordance with an embodiment.

FIG. 3 illustrates a bypass channel to a tear secretion measurement device. Device 300 includes capillary tube 306 with entrance end 302 and exit end 304. Inner surface 312 is mostly hydrophilic or a neutral hydrophile, and a small, localized inner surface 314 near exit end 304 is hydrophobic.

Larger tube 334 encompasses capillary tube 306, forming bypass channel 332 extending from entrance end 302 around an outside of capillary tube 306 to exit end 304. The ratio of the internal areas of internal tube 306 and larger tube 334 are selected so that a certain, predetermined ratio of liquid bypasses capillary tube 306 in bypass channel 332. For example, only 10% of the liquid flowing into the entrance of the larger tube may flow into capillary tube 306, leaving 90% to bypass it.

In some embodiments, the bypass channel is created through a tube that is about the same size as the sampling capillary tube or non-tube structure. For example, a non-tube structure can include a micromanufactured rectangular channel. In any case, a bypass channel may help with devices that are left in the eye for long periods of time.

Long-Term Tear Collecting Tube Device

A long-term tear collecting device's fiber-like geometry can be straight, curved, winding/twisting, etc. depending on its placement. For example, the microcapillary tube should have a curvature matching the curvature of the eyeball if it is placed inside the inferior eyelid for a few hours to a few months. In another example, the tube can also have a winding/twisting geometry to wrap around a punctal plug that will be inserted inside the punctal canal, and the tube will collect only a portion of the total tear going through both the punctal pug and the tube.

The tube should have a diameter to collect a portion of the total tear inside the inferior eyelid or through the punctal canal long-term wise in an eye, depending on the tear-collecting time. For example, a typical diameter can range from 10-3,000 µm.

The length of the tube collector, engineered together with its diameter, should be enough to collect the desirable portion of the all tear fluid inside the inferior eyelid or through the punctal canal. For example, a typical length can range from sub-millimeters to a few meters.

The interior surface of the tube collector is of neutral, that is, neither hydrophobic nor hydrophilic. This is a significant difference from the short-term tear collector. In other words, the water contact angle of the interior surface should be about 90±20 degrees so the meniscus force of the tear inside would be minimal and, therefore, only tear pressure from outside the entrance will push the tear to flow inside the tube collector.

The whole tube, including both ends of the entrance and exit, can be coated with a soft material, including but not limited to collagen or soft silicone, to ensure eye comfort.

One end of the tube maybe blocked with hydrophobic material.

The tube can also have a "lid" so after removal of tube the fluid inside does not evaporate. The tube can be replaced in a bag to further reduce the evaporation of the fluid from within the tube, whether the tube has a lid or not.

In theory, the tear liquid trapped inside either the long-term and short-term tear collectors can be measured by the device's weight change from an empty state. This would work especially well for the short-term tear collector. However, it may also be adequate to have a simple optical reader to measure the position of the meniscus inside the tear collector, which can be converted to the total volume of the tear, especially for the long-term collector.

After participating in a reading, both the long-term and short-term tear collector can be stored inside a sealed container so that the tear liquid will not evaporate and can be saved for future measurement and analysis. The reader can also read the various analytes and osmolarity of the tear fluid.

The inner diameter of the long-term tube may be between 1 μm-1 mm, among other diameters. The tube may be in a ring around the eye or coiled. The entrance to the coil is hydrophilic with the same values as those presented above for the short term embodiment. The middle of the tube can be neutral with a contact angle of 90°±15°. A hydrophobic coating on the exit would have a similar length and dimensions as the short term device, e.g., a contact angle of 91°-150°, and 1 μm-5 mm in diameter.

Wound in a coil, the outer diameter of this device can be as large as 25 mm, equivalent to some of the largest scleral lenses. The outer diameter may be as small as the 12 mm which places it at the edge of the cornea. The inner diameter may range from 11 mm to 24.5 mm. The device may be as thick as 2 mm, but preferably 1 mm thick at the most for comfort.

The inlet does not need to be a circle and may instead have multiple inlets or a long narrow slit to reduce the chance of clogging during use.

The inner coil diameter, corneal opening does not need to be circular. The opening can be elliptical to better match the opening between the eyelids.

Figure 4:
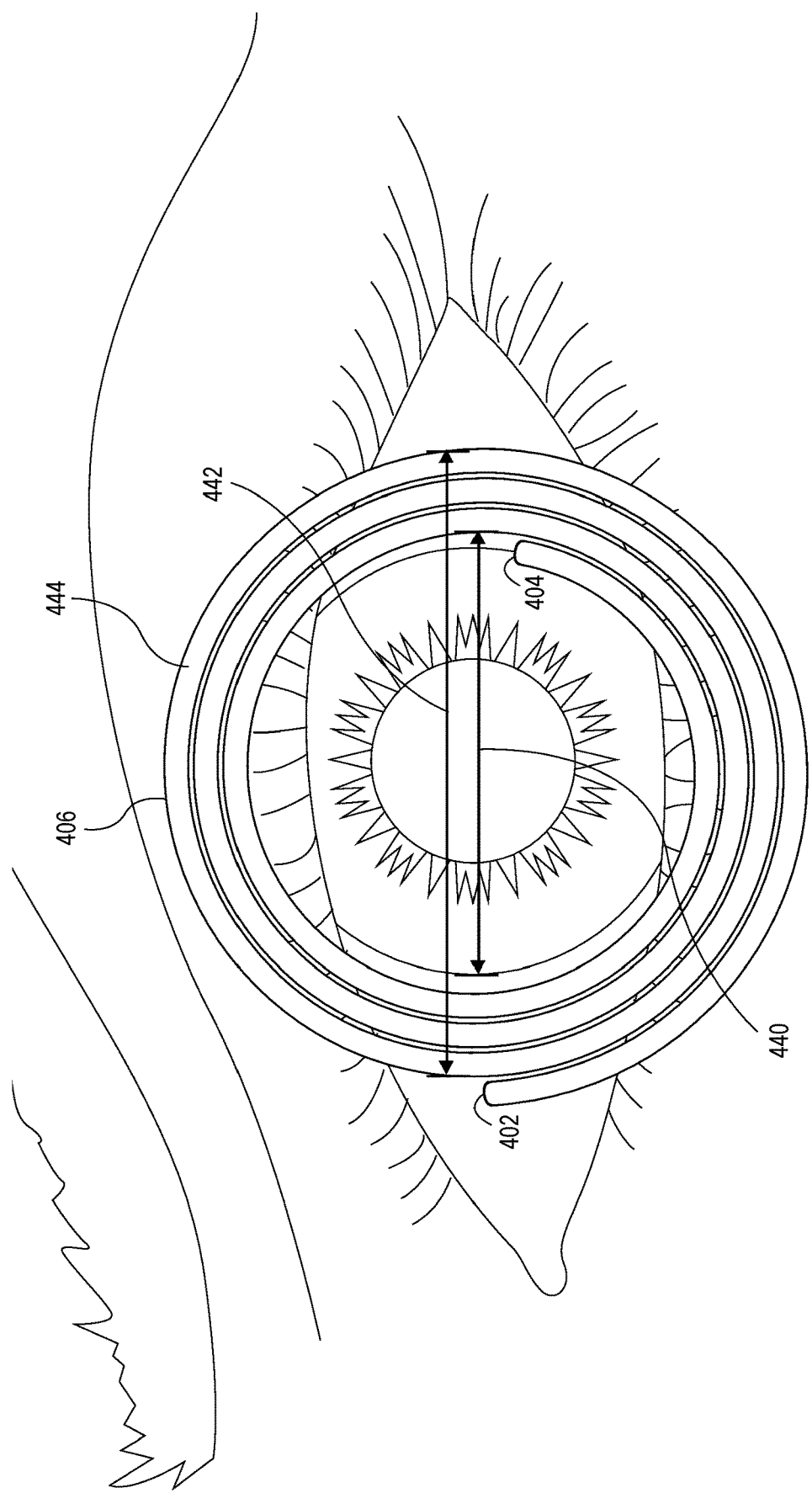
FIG. 4 illustrates a coiled tear measurement device on an eye in accordance with an embodiment.

FIG. 4 illustrates a circular coiled tear measurement device, which is a coil of capillary tube 406. Capillary tube has entrance end (inlet) 402 at the outside and exit end (outlet) 404 in the inside of the coil. The capillary tube is wound into a tight spiral forming coil 444 of inner diameter 440 and outer diameter 442.

The coil holds a significant volume of liquid that is collected from the lake of a patient's eye. Some embodiments include a bypass channel so that fluid may enter the tube and only a fraction of it is trapped in the capillary. The coil rings can be fused together as a common plastic element so that it is more manageable to insert and retrieve from the eye.

Coil 444 can be left in a patient's eye for long periods of time, sampling a percentage of the patient's tear fluid. With a bypass channel, the portion of the patient's tear fluid that is not trapped will flow back into the eye.

Figure 5:
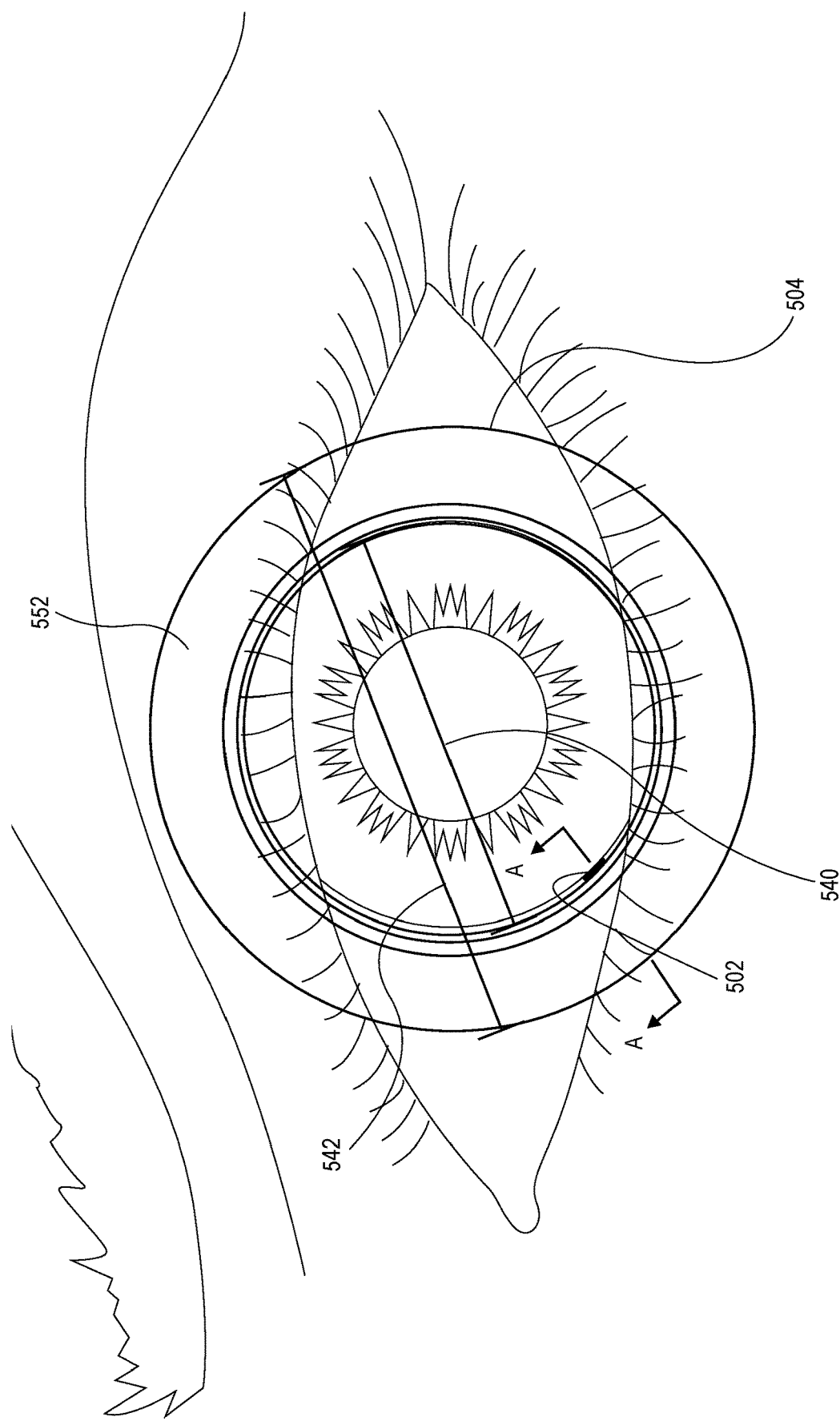
FIG. 5 illustrates a broad internal reservoir device on an eye in accordance with an embodiment.
Figure 6:
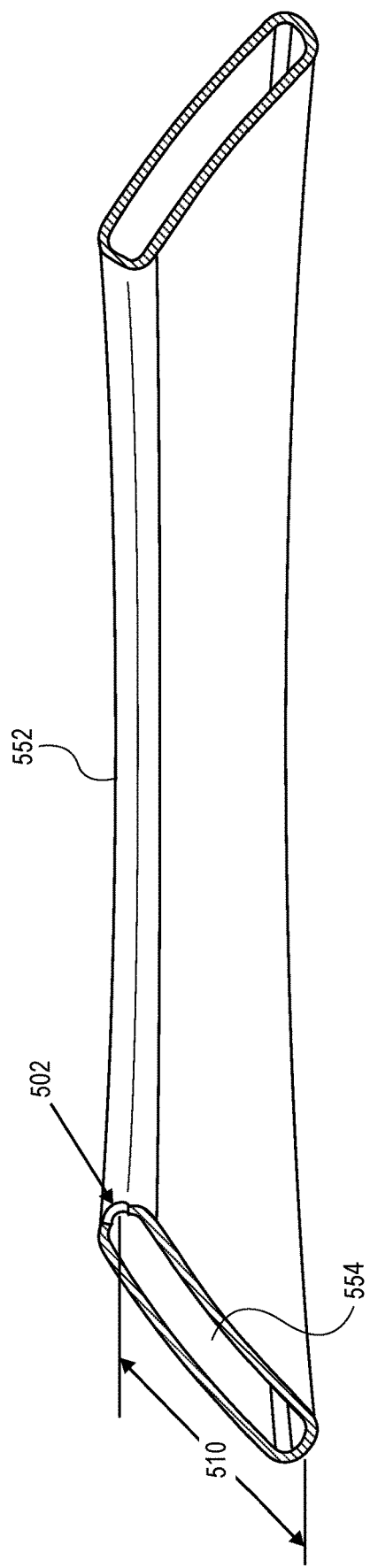
FIG. 6 is a cut out section of the device of FIG. 5.

FIGS. 5-6 illustrate a sclera-lens type of device 552 with broad internal reservoir 554. It has an entrance end (inlet) 502 at the center and an exit end (outlet) 504 on the outer diameter. In contrast to coiled-tube embodiments, the exemplary device is micromanufactured as a continuously open reservoir with an inner diameter 540 and outer diameter 542. The inlet 502 and outlet 504 are small compared with the large cross sectional area of the reservoir.

FIG. 6 shows a piece of the device with a wide radial cross section 510 of reservoir 554. The large cross section gives a large volume for tear secretion storage.

For thermo plastics such as polypropylene or polyether ether ketone (PEEK) the device can be manufactured using a hot spin cast mold, or by extrusion.

The internal shape of the device may also be produced out of wax, polypropylene carbonate (PPC), or photoresist, which may be made through lithographic processes or molding. These shapes can be coated in the desired polymer by either spray coating or chemical vapor deposition (CVD) in the case of parylene. The internal material may then be melted, thermally decomposed, or dissolved out of the shape.

Figure 7:
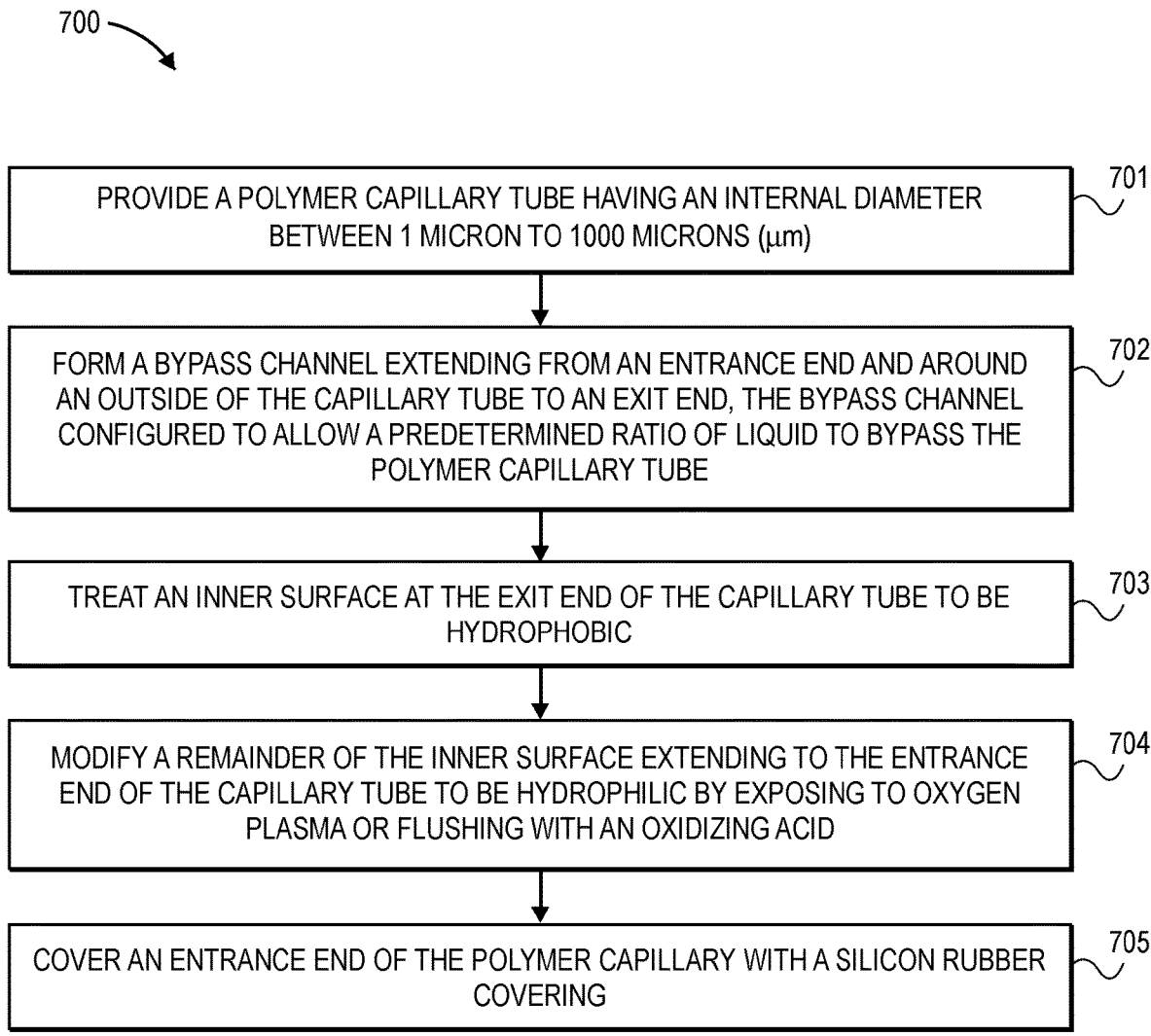
FIG. 7 is a flowchart illustrating a process in accordance with an embodiment.

FIG. 7 is a flowchart illustrating manufacturing process 700 in accordance with an embodiment. In operation 701, a polymer capillary tube having an internal diameter between 1 micro to 1000 microns (μm) is provided. In operation 702, a bypass channel is formed that extends from an entrance end around an outside of the capillary tube to an exit end of the capillary tube, the bypass channel being configured to allow a predetermined ratio of liquid to bypass the polymer capillary tube. In operation 703, an inner surface at the exit end of the capillary tube is treated to by hydrophobic. In operation 704, a remainder of the inner surface extending to the entrance end of the capillary tube is modified to be hydrophilic by exposing it to oxygen plasma or flushing it with an oxidizing acid. In operation 705, an entrance end of the polymer capillary is covered with a silicone rubber covering.

Figure 8:
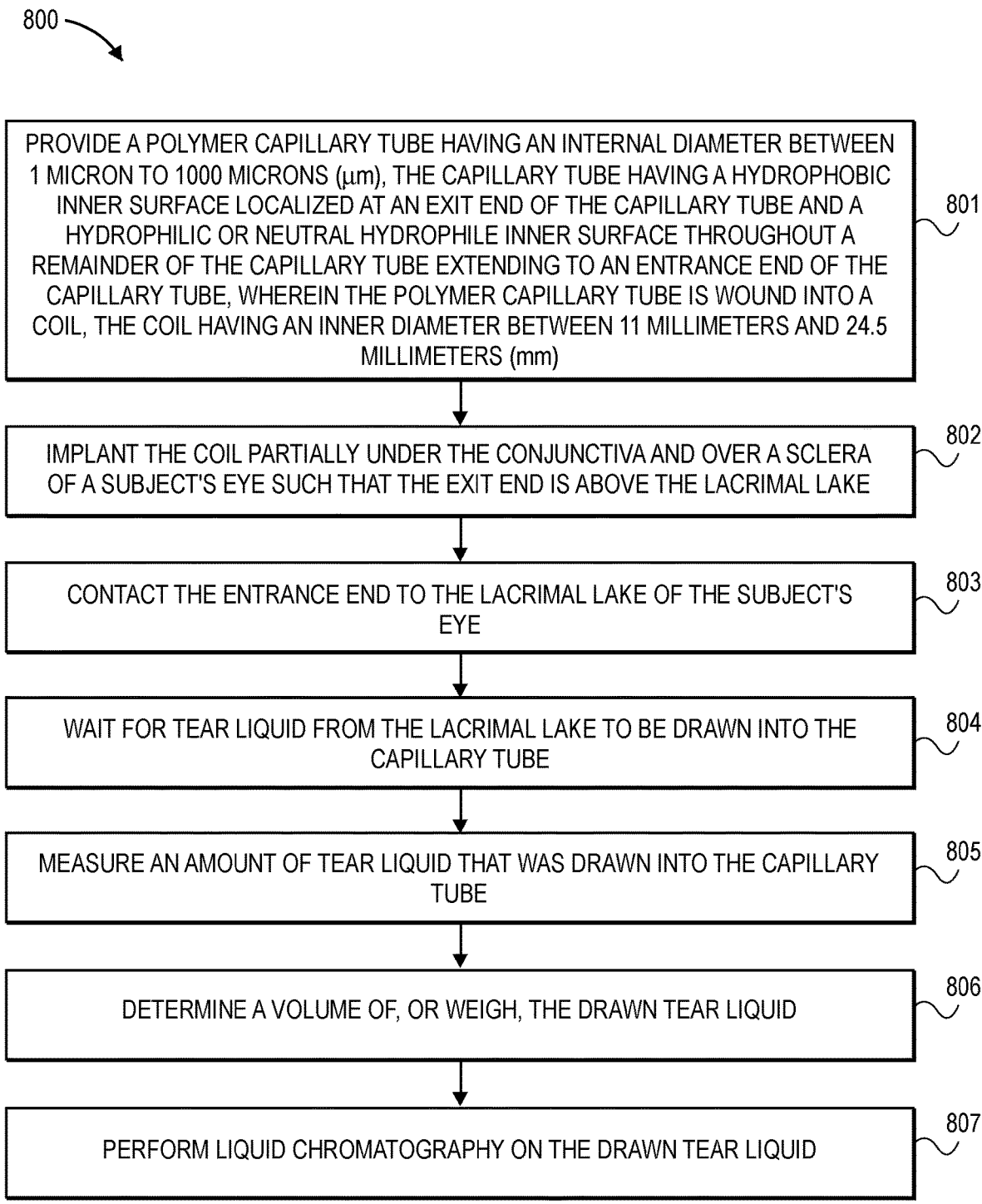
FIG. 8 is a flowchart illustrating a process in accordance with an embodiment.

FIG. 8 is a flowchart illustrating clinical use process 800 in accordance with an embodiment. In operation 801, a polymer capillary tube having an internal diameter between 1 micron to 1000 microns (μm) is provided, the capillary tube having a hydrophobic inner surface localized at an exit end of the capillary tube and a hydrophilic or neutral hydrophile inner surface throughout a remainder of the capillary tube extending to an entrance end of the capillary tube, wherein the polymer capillary tube is wound into a coil, the coil having an inner diameter between 11 millimeters and 24.5 millimeters (mm). In operation 802, the coil is implanted partially under the conjunctiva and over a sclera of a subject's eye such that the exit end is above the lacrimal lake of the eye. In operation 803, the entrance end is contacted to the lacrimal lake of the subject's eye. In operation 804, one waits for tear liquid from the lacrimal lake to be drawn into the capillary tube. This case be on the order of a few seconds, minutes, hours, days, weeks, or months. In operation 805, an amount of tear liquid that was drawn into the capillary tube is measured. In operation 806, a volume of the drawn tear liquid is determined, or it is weighed. In operation 807, liquid chromatography is performed on the drawn tear liquid.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain. "About" in reference to a temperature or other engineering units includes measurements or settings that are within ±1%, ±2%, ±5%, ±10%, or other tolerances of the specified engineering units as known in the art.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:

1. A tear secretion measurement apparatus comprising:
   a polymer capillary tube having an inner diameter between 1 micron to 1000 microns (µm), the capillary tube having a hydrophobic inner surface extending between 1 µm to 5000 µm from an exit end of the capillary tube and a hydrophilic or neutral hydrophile inner surface throughout a remainder of the capillary tube extending to an entrance end of the capillary tube.

2. The apparatus of claim 1 further comprising:
   a silicone rubber covering over an outer diameter of the capillary tube at the entrance end.

3. The apparatus of claim 1 wherein the inner diameter of the polymer capillary tube is between 200 µm and 400 µm.

4. The apparatus of claim 1 wherein the polymer capillary tube is biocompatible.

5. The apparatus of claim 1 wherein the polymer capillary tube comprises parylene C, parylene HT, polyamide, polyether ether ketone (PEEK), polyethylene, or polypropylene.

6. The apparatus of claim 1 wherein a length of the capillary tube is between 2 millimeters to 50 millimeters (mm) and the remainder of the inner surface is hydrophilic.

7. The apparatus of claim 2 wherein the silicone rubber covering is a pre-formed silicone tube into which the polymer capillary tube was inserted.

8. The apparatus of claim 2 wherein the silicone rubber covering was produced by dip coating the polymer capillary tube in diluted, uncured silicone rubber and allowing it to cure.

9. The apparatus of claim 2 wherein the silicone rubber covering extends over an entire outer diameter of the capillary tube from the entrance end to the exit end.

10. The apparatus of claim 1 wherein the capillary tube is transparent or translucent, the apparatus further comprising:
    volume measurement markings on an outer diameter of the capillary tube.

11. A tear secretion measurement apparatus comprising:
    a polymer capillary tube having an inner diameter between 1 micron to 1000 microns (µm), the capillary tube having a hydrophobic inner surface localized at an exit end of the capillary tube and a hydrophilic or neutral hydrophile inner surface throughout a remainder of the capillary tube extending to an entrance end of the capillary tube; and
    a bypass channel extending from the entrance end and around an outside of the capillary tube to the exit end, the bypass channel configured to allow a predetermined ratio of liquid to bypass the polymer capillary tube.

12. A tear secretion measurement apparatus comprising:
    a polymer capillary tube having an inner diameter between 1 micron to 1000 microns (µm), the capillary tube having a hydrophobic inner surface localized at an exit end of the capillary tube and a hydrophilic or neutral hydrophile inner surface throughout a remainder of the capillary tube extending to an entrance end of the capillary tube,
    wherein the polymer capillary tube is wound into a coil, the coil having an inner diameter between 11 millimeters and 24.5 millimeters (mm).

13. The apparatus of claim 12 wherein the wound capillary tube is fused to form a solid coil.

14. The apparatus of claim 12 further comprising:
    a silicone rubber covering over an outer diameter of the capillary tube at the entrance end.

15. The apparatus of claim 14 wherein the silicone rubber covering is a pre-formed silicone tube into which the polymer capillary tube was inserted.

16. The apparatus of claim 14 wherein the silicone rubber covering was produced by dip coating the polymer capillary tube in diluted, uncured silicone rubber and allowing it to cure.

17. The apparatus of claim 14 wherein the silicone rubber covering extends over an entire outer diameter of the capillary tube from the entrance end to the exit end.

18. The apparatus of claim 11 further comprising:
    a silicone rubber covering over an outer diameter of the capillary tube at the entrance end.

19. The apparatus of claim 18 wherein the silicone rubber covering is a pre-formed silicone tube into which the polymer capillary tube was inserted.

20. The apparatus of claim 18 wherein the silicone rubber covering was produced by dip coating the polymer capillary tube in diluted, uncured silicone rubber and allowing it to cure.

21. The apparatus of claim 18 wherein the silicone rubber covering extends over an entire outer diameter of the capillary tube from the entrance end to the exit end.

22. A tear secretion measurement apparatus comprising:
a polymer capillary tube having an inner diameter between 1 micron to 1000 microns (μm), the capillary tube having a hydrophobic inner surface extending between 0.001% to 10% of a length of the capillary tube from an exit end of the capillary tube and a hydrophilic or neutral hydrophile inner surface throughout a remainder of the capillary tube extending to an entrance end of the capillary tube.

23. The apparatus of claim 22 further comprising:
a silicone rubber covering over an outer diameter of the capillary tube at the entrance end.

24. The apparatus of claim 23 wherein the silicone rubber covering is a pre-formed silicone tube into which the polymer capillary tube was inserted.

25. The apparatus of claim 23 wherein the silicone rubber covering was produced by dip coating the polymer capillary tube in diluted, uncured silicone rubber and allowing it to cure.

26. The apparatus of claim 23 wherein the silicone rubber covering extends over an entire outer diameter of the capillary tube from the entrance end to the exit end.

\* \* \* \* \*